(12) United States Patent
Matsui et al.

(10) Patent No.: US 10,441,135 B2
(45) Date of Patent: Oct. 15, 2019

(54) ENDOSCOPE SYSTEM

(71) Applicant: OLYMPUS CORPORATION, Tokyo (JP)

(72) Inventors: Yasunori Matsui, Hino (JP); Shinji Yamashita, Tachikawa (JP); Yuzuru Tanabe, Niiza (JP); Yuta Matsuno, Hachioji (JP)

(73) Assignee: Olympus Corporation, Tokyo (JP)

( * ) Notice: Subject to any disclaimer, the term of this patent is extended or adjusted under 35 U.S.C. 154(b) by 262 days.

(21) Appl. No.: 15/446,559

(22) Filed: Mar. 1, 2017

(65) Prior Publication Data

US 2017/0172387 A1 Jun. 22, 2017

Related U.S. Application Data

(63) Continuation of application No. PCT/JP2016/053026, filed on Feb. 2, 2016.

(30) Foreign Application Priority Data

May 20, 2015 (JP) ................. 2015-103087

(51) Int. Cl.
*A61B 1/00* (2006.01)
*A61B 1/04* (2006.01)
(Continued)

(52) U.S. Cl.
CPC ...... *A61B 1/00087* (2013.01); *A61B 1/00006* (2013.01); *A61B 1/00009* (2013.01);
(Continued)

(58) Field of Classification Search
CPC . A61B 1/0661; A61B 1/0669; A61B 1/00087; A61B 1/00006; A61B 1/00009; A61B 1/045; A61B 1/063; A61B 1/06; H04N 5/2352; H04N 5/2354; H04N 5/243; H04N 2005/2255; H04N 5/2256
See application file for complete search history.

(56) References Cited

U.S. PATENT DOCUMENTS 4,928,172 A * 5/1990 Uehara ................. A61B 1/05
348/230.1
4,967,269 A * 10/1990 Sasagawa ............. A61B 1/042
348/230.1

(Continued)

FOREIGN PATENT DOCUMENTS

EP 1649801 A1 4/2006
JP 2006-115964 A 5/2006
(Continued)

OTHER PUBLICATIONS

International Search Report dated Apr. 26, 2016 issued in PCT/JP2016/053026.

*Primary Examiner* — John P Leubecker
*Assistant Examiner* — Shankar Raj Ghimire
(74) *Attorney, Agent, or Firm* — Scully Scott Murphy & Presser, P.C.

(57) ABSTRACT

An endoscope system includes an endoscope, an illumination portion, a light adjustment portion, an insertion channel configured to allow insertion of a laser probe capable of radiating an aiming monochromatic laser beam, a gain control portion, a halation detection portion, and a control portion, and in a case that halation by the aiming monochromatic laser beam is detected in the halation detection portion, the control portion controls the light adjustment portion to adjust the illumination light and controls the gain control portion to control the gain.

1 Claim, 8 Drawing Sheets

(51) Int. Cl.
  *A61B 1/06*    (2006.01)
  *A61B 1/018*   (2006.01)
  *A61B 1/045*   (2006.01)
  A61B 18/20    (2006.01)
  A61B 18/00    (2006.01)

(52) U.S. Cl.
  CPC .............. *A61B 1/018* (2013.01); *A61B 1/045* (2013.01); *A61B 1/063* (2013.01); *A61B 1/06* (2013.01); *A61B 18/20* (2013.01); *A61B 2018/00982* (2013.01); *A61B 2018/2025* (2013.01)

(56) References Cited

U.S. PATENT DOCUMENTS

| | | | |
|---|---|---|---|
| 6,545,703 B1 * | 4/2003 | Takahashi .......... | H04N 5/23209 348/625 |
| 6,724,418 B1 * | 4/2004 | Takahashi .............. | A61B 1/042 348/61 |
| 7,924,308 B2 * | 4/2011 | Abe ....................... | A61B 1/045 348/241 |
| 9,155,457 B2 * | 10/2015 | Yamashita ........... | A61B 1/0638 |
| 2006/0082646 A1 | 4/2006 | Abe et al. | |
| 2007/0076975 A1 | 4/2007 | Abe | |
| 2012/0078046 A1 * | 3/2012 | Sasaki ................ | A61B 1/00009 600/109 |

FOREIGN PATENT DOCUMENTS

| | | |
|---|---|---|
| JP | 2007-097711 A | 4/2007 |
| JP | 2009-118988 A | 6/2009 |
| JP | 2009-288682 A | 12/2009 |
| JP | 2012-065945 A | 4/2012 |

* cited by examiner

ENDOSCOPE SYSTEM

CROSS REFERENCE TO RELATED APPLICATION

This application is a continuation application of PCT/JP2016/053026 filed on Feb. 2, 2016 and claims benefit of Japanese Application No. 2015-103087 filed in Japan on May 20, 2015, the entire contents of which are incorporated herein by this reference.

BACKGROUND OF THE INVENTION

1. Field of the Invention

The present invention relates to an endoscope system, for example, an endoscope system that includes an image pickup portion capable of outputting an observation image of an object as an image signal and allows a laser probe to be utilized.

2. Description of the Related Art

Conventionally, in a medical field and an industrial field, an endoscope including an image pickup portion that observes a subject is widely used. In addition, a technology of configuring an endoscope system in which various kinds of signal processing relating to an endoscope are borne by a signal processor called a video processor freely attachably and detachably connected to the endoscope is also known.

On the other hand, in recent years, in a urological field, an endoscopic procedure has been taken for urinary stones which are stones generated inside a kidney and stuck in a ureter or a urethra.

For the endoscopic procedure, specifically, the procedure is known in which a laser probe connected to a YAG laser device is inserted to an insertion channel formed in an insertion portion of an endoscope and stones stuck in the ureter for example are irradiated with the YAG laser thereafter, thereby breaking and collecting the stones, for example (see Japanese Patent Application Laid-Open Publication No. 2009-288682).

Incidentally, since a laser beam such as a so-called YAG laser radiated from the laser probe as described above is invisible light, a visible light laser (hereinafter, an aiming laser) for irradiation position confirmation is radiated before the YAG laser for lithotripsy irradiation is radiated in order to make it easy to confirm an irradiation position of a lithotripsy target (see Japanese Patent Application Laid-Open Publication No. 2009-288682).

SUMMARY OF THE INVENTION

An endoscope system of one aspect of the present invention includes: an endoscope including an image pickup device configured to pick up an image of an object; an illumination portion configured to irradiate the object with illumination light; a light adjustment portion configured to control illumination light intensity and irradiation time period from the illumination portion; an insertion channel provided in the endoscope and configured to allow insertion of at least a laser probe capable of irradiating a predetermined position of the object with an aiming monochromatic laser beam for confirming a laser irradiation position; a gain control portion configured to control a gain of image pickup signals outputted from the image pickup device; a halation detection portion configured to detect halation relating to the object when the aiming monochromatic laser beam is radiated; and a control portion configured to control at least the light adjustment portion and the gain control portion, and in a case that the halation by the aiming monochromatic laser beam is detected in the halation detection portion, the control portion controls the light adjustment portion to adjust the illumination light and controls the gain control portion to control the gain.

DETAILED DESCRIPTION OF THE PREFERRED EMBODIMENT(S)

Hereinafter, embodiments of the present invention will be described with reference to the drawings.

In addition, the invention is not limited by the embodiments. Further, in descriptions of the drawings, same signs are attached to same parts. Still further, note that the drawings are schematic and that a relation between a thickness and a width of individual members and a ratio of the respective members or the like are different from the actual ones. In addition, even among the drawings, a part where mutual dimensions or the ratio is different is included.

Figure 1:
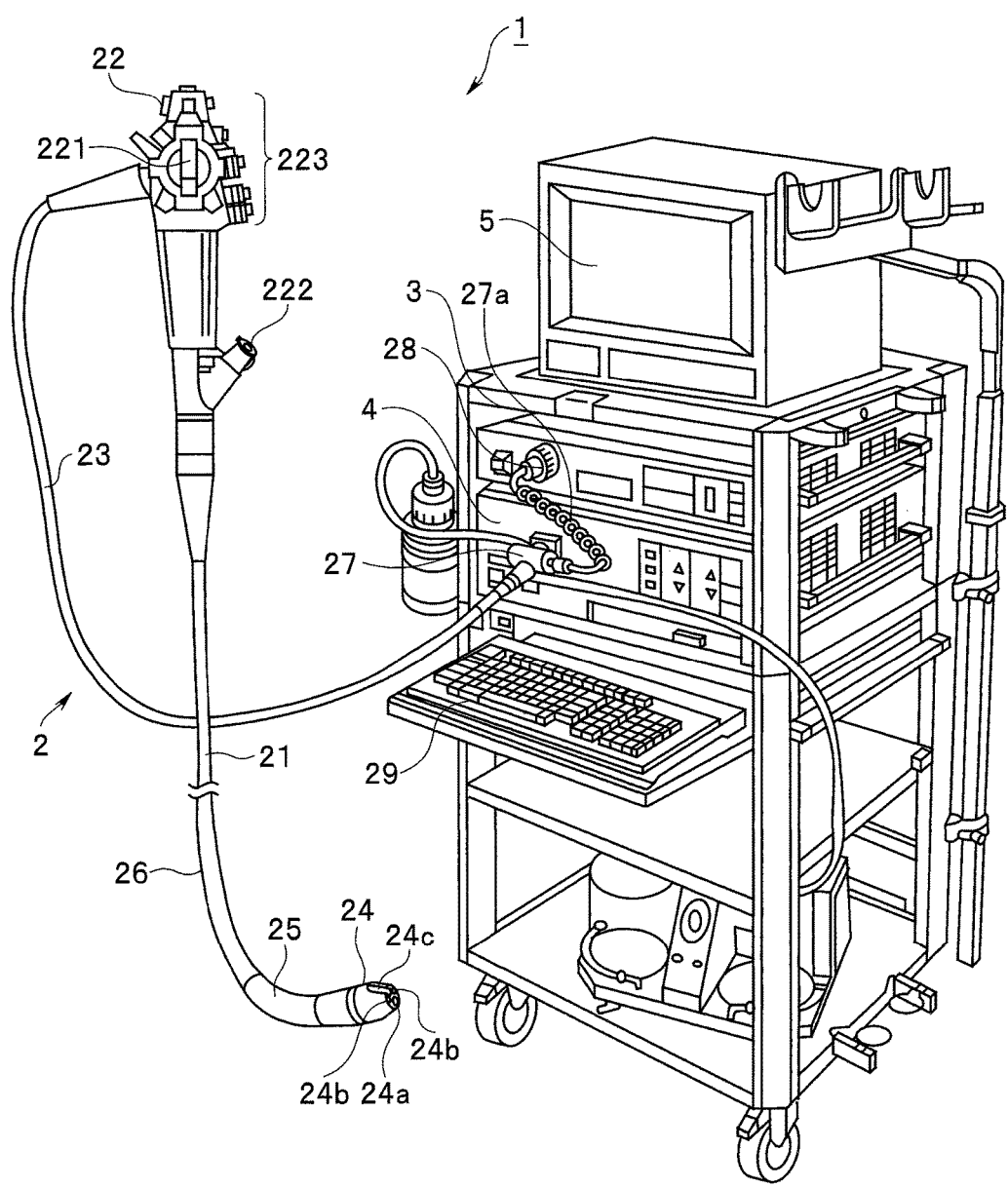
FIG. 1 is a perspective view illustrating a schematic configuration of an endoscope system relating to a first embodiment of the present invention.
Figure 2:
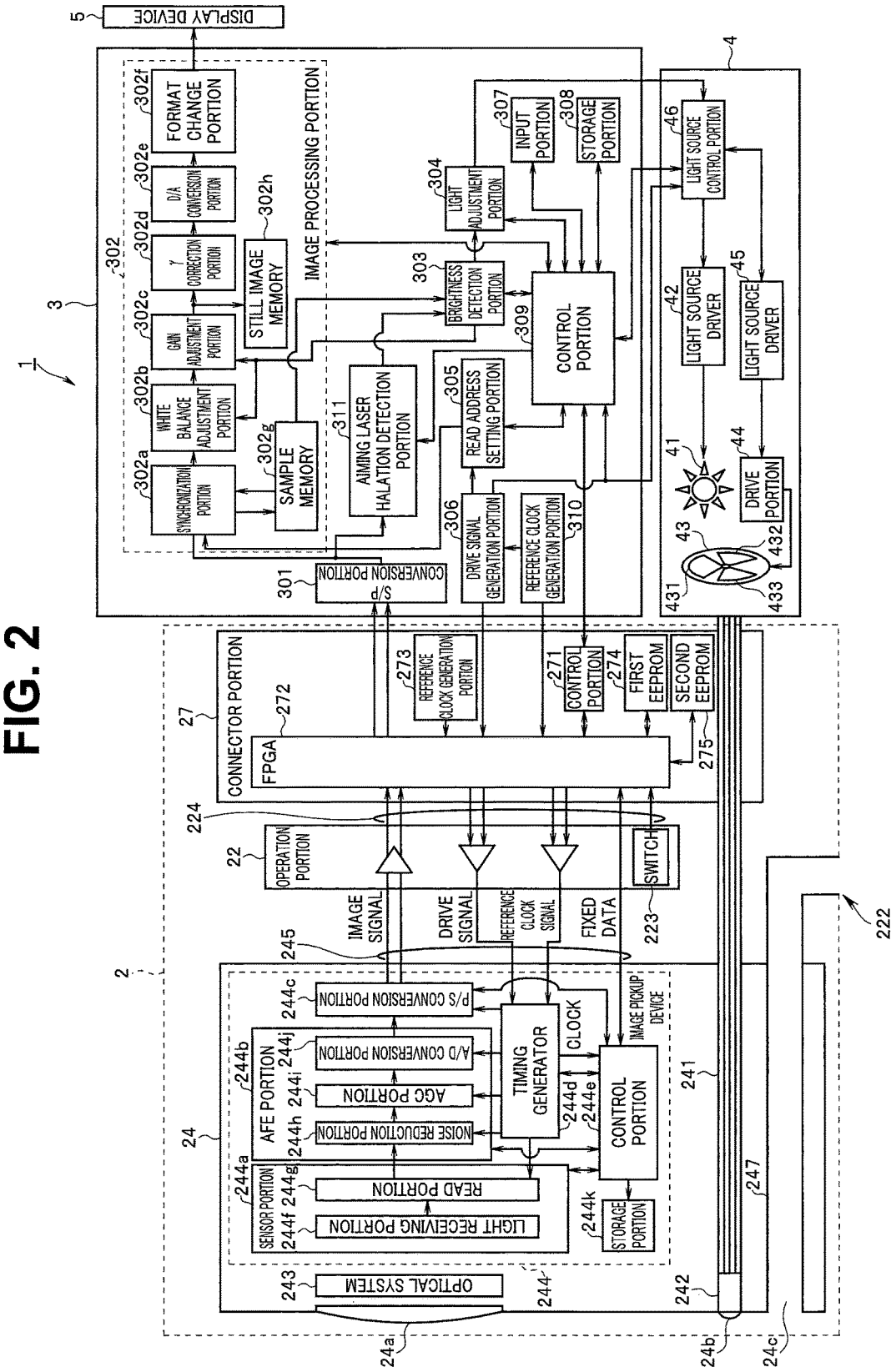
FIG. 2 is a block diagram illustrating a functional configuration of a main portion of the endoscope system relating to the first embodiment.

FIG. 1 is a perspective view illustrating a schematic configuration of an endoscope system relating to a first embodiment of the present invention, and FIG. 2 is a block diagram illustrating a functional configuration of a main portion of the endoscope system relating to the first embodiment.

Figure 3:
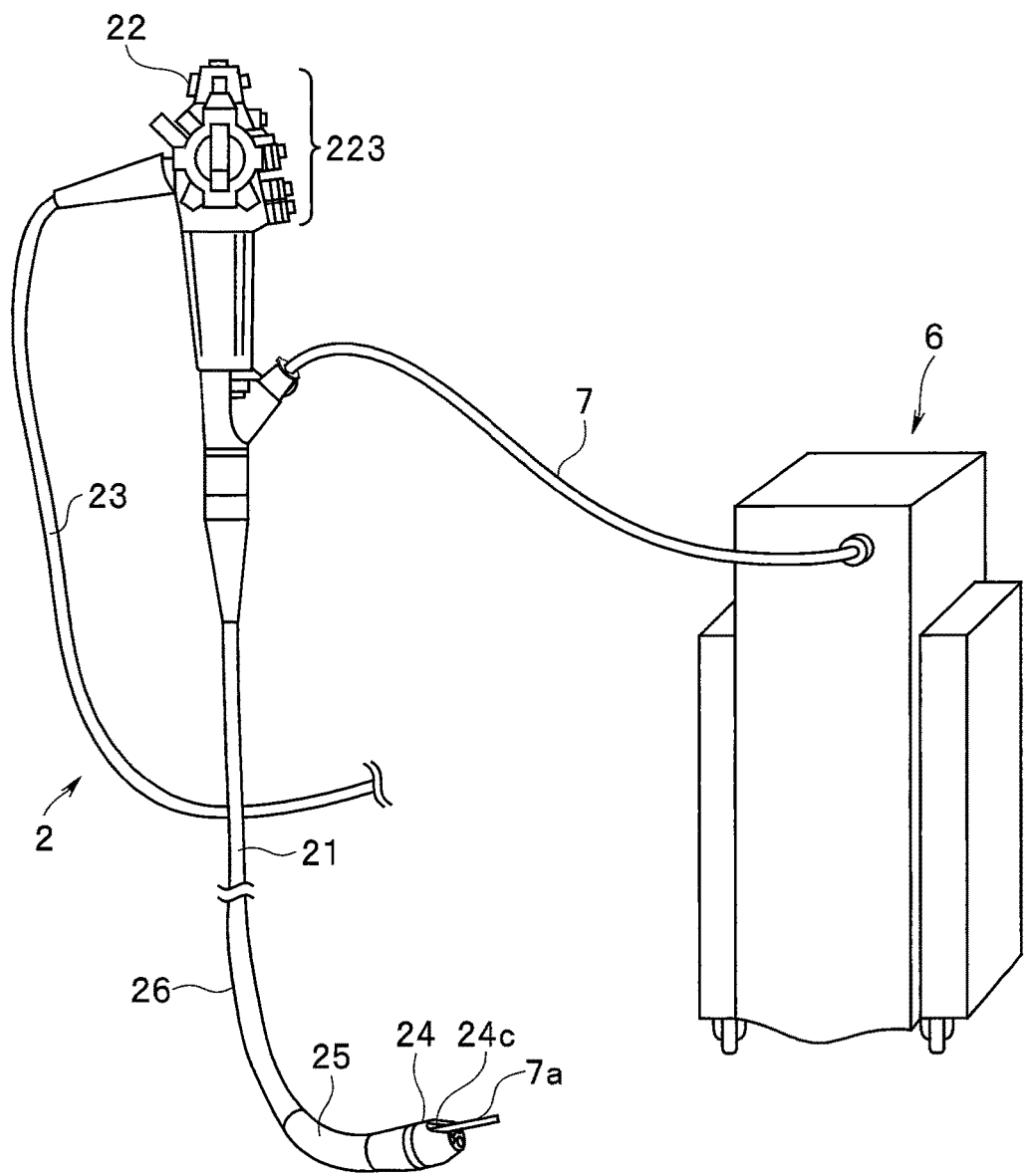
FIG. 3 is a main portion perspective view illustrating a state when a laser probe is inserted from a laser device to the endoscope system relating to the first embodiment.
Figure 4:
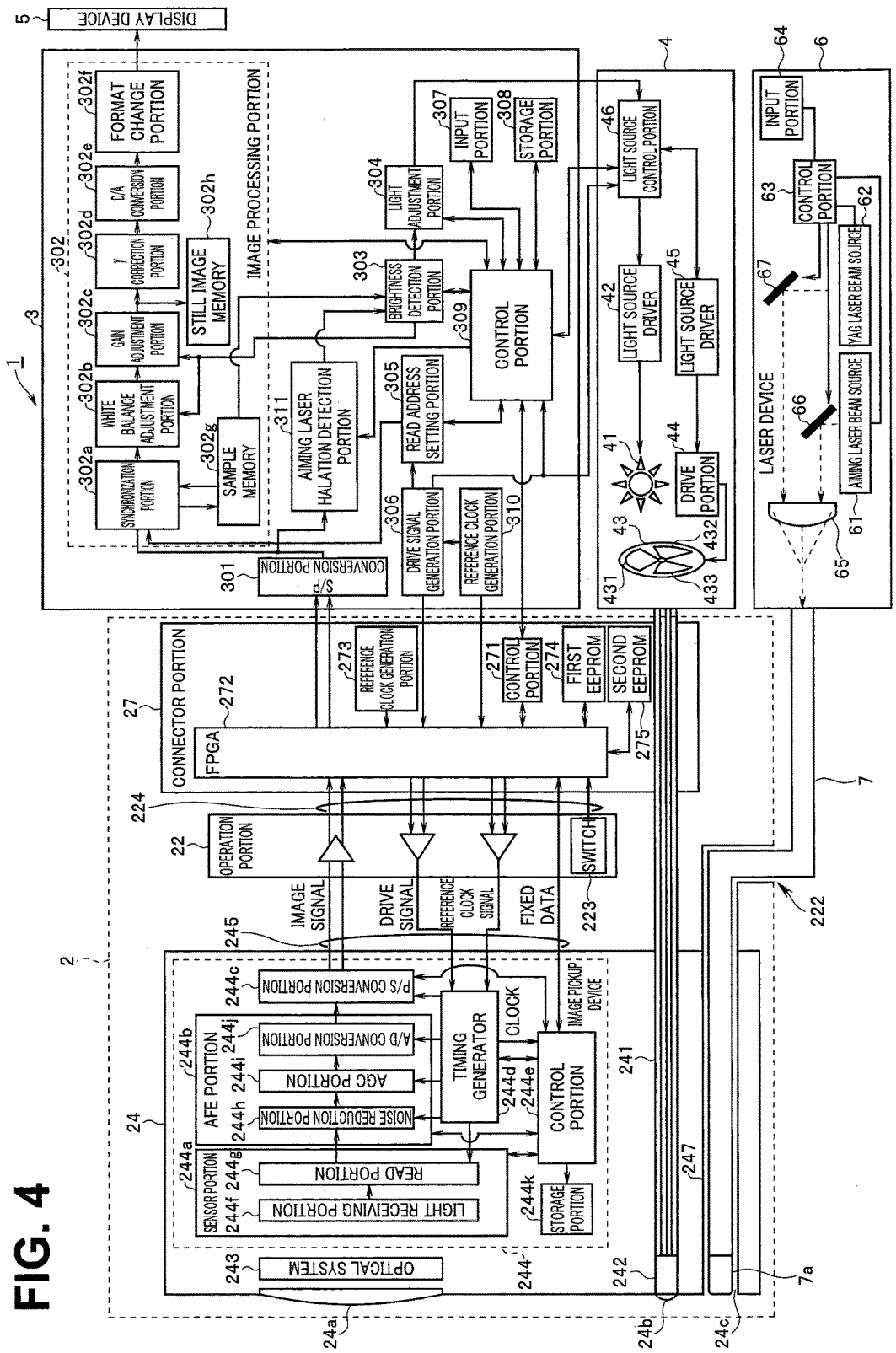
FIG. 4 is a block diagram illustrating a functional configuration of the main portion when the laser probe connected to the laser device is inserted to the endoscope system relating to the first embodiment.

Further, FIG. 3 is a main portion perspective view illustrating a state when a laser probe is inserted from a laser device to the endoscope system relating to the first embodiment, and FIG. 4 is a block diagram illustrating a functional configuration of the main portion when the laser probe is inserted from the laser device to the endoscope system relating to the first embodiment.

As illustrated in FIG. 1 and FIG. 2, an endoscope system 1 includes: an endoscope 2 configured to pick up an in-vivo image of an object and output an image signal of the object image by inserting a distal end portion into a body cavity of a subject; a video processor 3 configured to execute predetermined image processing to the image signals outputted from the endoscope 2 and generally control an operation of the entire endoscope system 1; a light source device 4 configured to generate illumination light to be emitted from a distal end of the endoscope 2; and a display device 5 configured to display an image to which the image processing is executed in the video processor 3.

In addition, as illustrated in FIG. 3 and FIG. 4, to the endoscope 2 in the endoscope system 1 in the present embodiment, a laser probe 7 connected to a laser device 6 that generates a YAG laser beam and an aiming monochromatic laser beam, that is, the laser probe 7 capable of radiating the YAG laser beam and the aiming monochromatic laser beam is inserted. The laser probe 7 will be described in detail later.

The laser device 6 includes a YAG laser beam source that generates a laser beam configured to break a target existing at a predetermined position of the object and an aiming laser beam source that generates the aiming monochromatic laser beam for confirming a laser irradiation position by the YAG laser, and details will be described later.

Returning to FIG. 1 and FIG. 2, the endoscope 2 is a so-called cystopyelography video scope, and includes an insertion portion 21 configured to have flexibility and form an elongate shape, an operation portion 22 connected to a proximal end side of the insertion portion 21 and configured to receive input of various kinds of operation signals, and a universal cord 23 extended from the operation portion 22 and incorporating various kinds of cables connecting the video processor 3 and the light source device 4.

The insertion portion 21 includes a distal end portion 24 incorporating an image pickup device to be described later, a bending portion 25 formed of fluororubber for example and configured to be freely bendable in two upper and lower directions, and a flexible and long-length soft tube portion 26 connected to the proximal end side of the bending portion 25 and formed of fluororesin for example.

Figure 5:
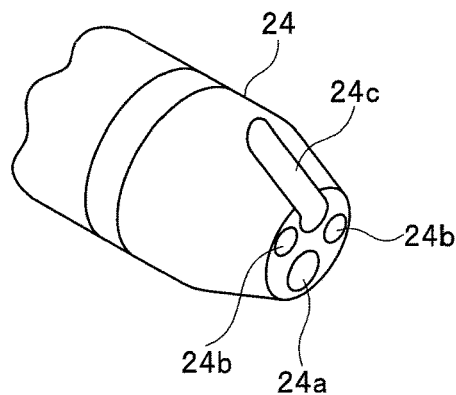
FIG. 5 is a main portion enlarged perspective view illustrating a configuration of a distal end portion of an endoscope insertion portion in the endoscope system relating to the first embodiment.

The distal end portion 24 is configured using polysulfone or the like for example, and includes, as illustrated in FIG. 1, FIG. 2 and FIG. 5, a light guide 241 forming a light guide path of light generated by the light source device 4, an illumination lens 242 that is an illumination portion provided on a distal end of the light guide 241, an illumination lens window 24b disposed on the distal end side of the illumination lens 242, an objective lens 24a configured to converge the object image, an objective optical system 243 including the objective lens 24a, an image pickup device 244 as an image pickup apparatus provided on an image forming position of the objective optical system 243 and configured to receive the light converged by the objective optical system 243, photoelectrically convert the light to electric signals and execute predetermined signal processing, a treatment instrument channel 247 to which a treatment instrument such as the laser probe 7 described above is inserted, and a distal end opening portion 24c of the treatment instrument channel 247.

Referring to FIG. 2, an electric configuration of the image pickup device 244 will be described.

As illustrated in FIG. 2, the image pickup device 244 includes a sensor portion 244a (image pickup portion) configured to photoelectrically convert the light from the objective optical system 243 and output the electric signals as image information, an analog front end 244b (hereinafter, referred to as "AFE portion 244b") configured to perform noise elimination and A/D conversion to the electric signals outputted by the sensor portion 244a, a P/S conversion portion 244c (transmission portion) configured to parallel/serial convert digital signals outputted by the AFE portion 244b and transmit the signals to outside, a timing generator 244d (synchronizing signal generation portion) configured to generate a pulse of drive timing of the sensor portion 244a and a pulse of various kinds of signal processing in the AFE portion 244b and the P/S conversion portion 244c, a control portion 244e configured to control an operation of the image pickup device 244, and a storage portion 244k configured to store various kinds of setting information.

The image pickup device 244 adopts a CMOS (complementary metal oxide semiconductor) image sensor (CIS) in the present embodiment. The timing generator 244d receives various kinds of drive signals (synchronizing signals) transmitted from the video processor 3.

The sensor portion 244a includes a light receiving portion 244f where a plurality of pixels each including a photodiode that stores electric charges according to a light quantity and an amplifier that amplifies the electric charges stored by the photodiode are disposed in a two-dimensional matrix shape, and a read portion 244g configured to read the electric signals generated by the pixel arbitrarily set as a read target among the plurality of pixels in the light receiving portion 244f as the image information.

The AFE portion 244b includes a noise reduction portion 244h configured to reduce noise components included in the electric signals (analog), an AGC (auto gain control) portion 244i configured to adjust an amplification factor (gain) of the electric signals and maintain a constant output level, and an A/D conversion portion 244j configured to A/D convert the electric signals outputted through the AGC portion 244i. The noise reduction portion 244h reduces noise using a correlated double sampling method for example.

The control portion 244e controls various kinds of operations of the distal end portion 24 according to setting data received from the video processor 3. Note that the control portion 244e is configured using a CPU or the like.

The storage portion 244k is realized using a semiconductor memory such as a flash memory or a DRAM (dynamic random access memory) in the present embodiment, and stores identification information and observation information indicating an observation system of a field sequential system or a synchronous system (note that the video processor 3 adopts a field sequential observation system in the present embodiment) of the video processor 3, an image pickup speed (frame rate) of the image pickup device 244, and a read speed or a shutter control setting of pixel information from an arbitrary pixel of the sensor portion 244a and transmission control information of the pixel information read by the AFE portion 244b or the like.

A cable assembly 245 for which a plurality of signal lines that transmit and receive the electric signals to/from the video processor 3 are bundled is connected between the operation portion 22 and the distal end portion 24, and a cable assembly 224 is connected between the operation portion 22 and a connector portion 27. Note that the plurality signal lines include the signal line that transmits the image signals outputted by the image pickup device 244 to the video processor 3 and the signal line that transmits control signals outputted by the video processor 3 to the image pickup device 244 or the like.

In addition, in the present embodiment, a system (differential transmission) of transmitting one signal using two signal lines (differential signal lines) is used for transmission and reception of the electric signals. Since noise can be canceled even when the noise is mixed in the individual lines by turning voltages between the differential signal lines to be positive (+) and negative (−, phase inversion) respectively, the differential transmission system is strong against the noise compared to single end signals and enables high speed transmission of data.

Note that it is preferable to use the differential transmission described above in the case that a length of the universal cord 23 or the soft tube portion 26 is long, however, in the case that the length is short, single end signal transmission using the single end signal is also applicable.

Returning to FIG. 1, the operation portion 22 includes a bending knob 221 configured to bend the bending portion 25 in the upper and lower directions, a treatment instrument insertion portion 222 configured to insert at least a treatment instrument such as the laser probe 7, and a switch 223 including a plurality of input switches that input signals of switching air feeding means or water feeding means or the like and setting of the video processor 3 or the light source device 4.

In the present embodiment, when the laser probe 7 is inserted from the treatment instrument insertion portion 222, a distal end portion 7a of the laser probe 7 appears from the distal end opening portion 24c of the distal end portion 24 through the treatment instrument channel 247 of the distal end portion 24.

On the other hand, in the present embodiment, in the case of transmitting the signals from the connector portion 27 to the distal end portion 24, the signals are intermediated by the universal cord 23 and a circuit that converts differential signals to the single end signals is disposed.

Here, in the case of transmitting the differential signals to the distal end portion 24, a conversion circuit that converts the differential signals to the single end signals may be a differential buffer, or the differential signals to be transmitted from the distal end portion 24 to the connector portion 27 may be intermediated by the operation portion 22 once and the differential buffer may be arranged.

Note that, for example, it is preferable to configure the insertion portion 21 and the universal cord 23 by image pickup cables suitable for respective transmission such as applying a twin-ax line for differential signal transmission inside the universal cord 23 and a coaxial line for single end signal transmission inside the insertion portion 21.

The universal cord 23 incorporates at least the light guide 241 and the cable assembly 224. The universal cord 23 includes the connector portion 27 (see FIG. 1) freely attachable and detachable to/from the light source device 4.

For the connector portion 27, a coil-like coil cable 27a is extended, and an electric connector portion 28 freely attachable and detachable to/from the video processor 3 is provided on an extension end of the coil cable 27a.

The connector portion 27 includes in inside a control portion 271 configured to control the endoscope 2, an FPGA (field programmable gate array) 272, a reference clock generation portion 273 configured to generate a reference clock signal (for example, a clock of 68 MHz) to be a reference of the operation of various components of the endoscope 2, a first EEPROM 274 configured to record configuration data, and a second EEPROM 275 configured to record endoscope intrinsic data including image pickup information.

Next, a configuration of the video processor 3 will be described.

The video processor 3 is configured including an S/P conversion portion 301, an image processing portion 302, a brightness detection portion 303, a light adjustment portion 304, a read address setting portion 305, a drive signal generation portion 306, an input portion 307, a storage portion 308, a control portion 309, a reference clock generation portion 310, and an aiming laser halation detection portion 311.

Note that, in the present embodiment, the configuration of adopting the field sequential system as the video processor 3 is described as an example, however, the present invention is applicable also for the synchronous system (see a second embodiment for the synchronous system).

The S/P conversion portion 301 serial/parallel converts the image signals (digital signals) outputted from the endoscope 2 when the endoscope 2 is connected to the video processor 3.

The image processing portion 302 executes predetermined image processing to the image signals of a parallel form outputted from the S/P conversion portion 301, and generates an in-vivo image to be displayed by the display device 5. In addition, the image processing portion 302 includes a synchronization portion 302a, a white balance (WB) adjustment portion 302b, a gain adjustment portion 302c which is a gain control portion, a γ correction portion 302d, a D/A conversion portion 302e, a format change portion 302f, a sample memory 302g, and a still image memory 302h.

The synchronization portion 302a inputs the image signals inputted as the pixel information to three memories (not shown in the figure) provided for each pixel, holds values of the individual memories while successively updating the values corresponding to addresses of the pixels of the light receiving portion 244f read by the read portion 244g, and synchronizes the image signals of the three memories as RGB image signals.

In addition, the synchronization portion 302a successively outputs the synchronized RGB image signals to the white balance adjustment portion 302b, and outputs part of RGB image signals to the sample memory 302g for image analysis of brightness detection or the like.

The white balance adjustment portion 302b automatically adjusts a white balance of the RGB image signals. Specifically, the white balance adjustment portion 302b automatically adjusts the white balance of the RGB image signals based on a color temperature included in the RGB image signals.

The gain adjustment portion 302c adjusts the gain of the RGB image signals. The gain adjustment portion 302c outputs the gain-adjusted RGB signals to the γ correction portion 302d, and outputs part of RGB image signals to the still image memory 302h for still image display. Note that details will be described later.

The γ correction portion 302d performs gradation correction (γ correction) of the RGB image signals corresponding to the display device 5.

The D/A conversion portion 302e converts the image signals outputted by the γ correction portion 302d to analog signals.

The format change portion 302f changes the image signals converted to the analog signals to a file format for moving images such as a high vision system and outputs the signals to the display device 5.

<Halation Detection Function when Aiming Laser is Radiated>

Next, a configuration relating to a halation detection function when an aiming laser is radiated in the video processor 3 will be described.

The aiming laser halation detection portion 311 is a circuit that characterizes the present invention, and is a circuit that detects halation of the object when the aiming laser is radiated from the laser probe 7 inserted to the insertion channel 247 in the endoscope 2.

In addition, the aiming laser halation detection portion 311 holds the RGB image signals before being synchronized in the synchronization portion 302a respectively in an internal memory based on timing control signals outputted from the control portion 309.

Here, of the RGB image signals held in the internal memory in the aiming laser halation detection portion 311, when a signal level of "R" is defined as "Rs", a signal level of "G" is defined as "Gs" and a signal level of "B" is defined as "Bs", the aiming laser halation detection portion 311 detects the halation by the aiming laser of "R" single color from "Rs/Gs" which is a luminance level ratio of "Rs" and "Gs" and "Rs/Bs" which is a luminance level ratio of "Rs" and "Bs".

That is, first, a stipulated level value of the signal level "Rs" of R at which a luminance level causes the halation on a monitor screen is defined as "Rs_full", and the stipulated level values of the luminance level ratios "Rs/Gs" and "Rs/Bs" to be recognized as the aiming laser beam are defined as "RGaim_ratio" and "RBaim_ratio" respectively.

Note that the stipulated level values "Rs_full", "RGaim_ratio" and "RBaim_ratio" are specific values determined by a light source light quantity or an image pickup signal gain for each endoscope system, and in the present embodiment, held (not shown in the figure) as parameters inside the control portion 309.

Then, in the case that the R signal level "Rs" of the RGB image signals and the luminance level ratios "Rs/Gs" and "Rs/Bs" both exceed the stipulated level values described above, the aiming laser halation detection portion 311 detects the case as the halation by the aiming laser beam, and outputs halation information by the aiming laser to the brightness detection portion 303.

<Brightness Control Function when Aiming Laser is Radiated>

Next, a configuration relating to a brightness control function when the aiming laser is radiated in the video processor 3 will be described.

The brightness detection portion 303 detects a brightness level corresponding to the individual pixels from the RGB image signals held by the sample memory 302g, records the detected brightness level in a memory provided inside and also outputs the level to the control portion 309.

In addition, under control of the control portion 309, the brightness detection portion 303 calculates a white balance adjustment value, a gain adjustment value and a light irradiation amount value to be target brightness based on the detected brightness level, and outputs the white balance adjustment value to the white balance adjustment portion 302b, the gain adjustment value to the gain adjustment portion 302c, and the light irradiation amount value to the light adjustment portion 304.

Here, for output control of the gain adjustment value and the light irradiation amount value by the brightness detection portion 303 under the control of the control portion 309, the light irradiation amount value is given priority. Then, under the control of the control portion 309, the brightness detection portion 303 performs the control to raise the light irradiation amount value in the case that the brightness lacks, and performs the control to raise the gain adjustment value in the case that a target value of the brightness is not reached yet.

In addition, in the present embodiment, the brightness detection portion 303 performs the control to change the ratio of the gain adjustment value and the light irradiation amount value in a light adjustment operation to perform the operation based on the halation information from the aiming laser halation detection portion 311.

That is, in the case that the aiming laser halation detection portion 311 detects the halation, under the control of the control portion 309, the brightness detection portion 303 controls the output of the gain adjustment value so as to lower the gain of the gain adjustment portion 302c (apply a negative direction gain depending on a situation) until the level of the aiming laser halation is lowered to a constant level, and raises the light irradiation amount value to be outputted to the light adjustment portion 304, thereby performing the control to turn the brightness of the display image to a target level.

Further, the brightness detection portion 303 does not perform the control described above (the gain of the gain adjustment portion 302c is a positive direction gain) in the case that the aiming laser halation level is equal to or below a stipulated value, and controls the gain adjustment value of the gain adjustment portion 302c and the light irradiation amount of the light adjustment portion 304 so that the brightness reaches the target level.

In addition, under the control of the control portion 309, the light adjustment portion 304 sets a type, a light quantity and light emission timing or the like of the light generated by the light source device 4 based on the light irradiation amount value calculated by the brightness detection portion 303, and transmits light source synchronizing signals including the set condition to the light source device 4.

In addition, the read address setting portion 305 has a function of setting read target pixels and a read order on a light receiving surface of the sensor portion 244a by communicating with the control portion 271 in the endoscope 2 under the control of the control portion 309. At the time, the control portion 271 in the endoscope 2 reads kind information of the sensor portion 244a stored in the second EEPROM 275, and transmits the information to the video processor 3.

In addition, the read address setting portion 305 has a function of setting the address of the pixel of the sensor portion 244a read by the AFE portion 244b. Then, the read address setting portion 305 outputs the set address information of the read target pixel to the synchronization portion 302a.

The drive signal generation portion 306 generates timing signals for drive (horizontal synchronizing signals (HD) and vertical synchronizing signals (VD)) for driving the endoscope 2, and transmits the timing signals through the FPGA 272, and predetermined signal lines included in the cable assemblies 224 and 245 to the timing generator 244d (image pickup device 244). The timing signals include the address information of the read target pixel.

In addition, the drive signal generation portion 306 generates standby signals for performing transmission control of the electric signals transmitted from the endoscope 2 to the video processor 3. Here, the standby signals are signals that set the transmission to the side of the FPGA 272 of the electric signals (image information) by the P/S conversion portion 244c to either one of a transmission state and a stop state (standby state).

The input portion 307 receives input of operation instruction signals that instruct the operation of the endoscope system 1 such as freeze and release set by a front panel or a keyboard.

The storage portion 308 is realized using a semiconductor memory such as a flash memory or a DRAM (dynamic random access memory). The storage portion 308 stores various kinds of programs for operating the endoscope system 1 and data including various kinds of parameters needed for the operation of the endoscope system 1 or the like.

In addition, the storage portion 308 stores the identification information and the observation information of the video processor 3. Here, the identification information includes intrinsic information (ID) of the video processor 3, a model year, spec information of the control portion 309 and transmission rate information.

The control portion 309 is configured using a CPU or the like, and performs drive control of the individual components including the video processor 3 (the aiming laser halation detection portion 311 in particular), the endoscope 2 and the light source device 4, and input/output control of information to the individual components or the like.

In addition, the control portion 309 transmits the setting data for image pickup control to the FPGA 272 of the connector portion 27 in the endoscope 2 connected to the video processor 3, and transmits the signals and the data needed for the image pickup device 244 through the predetermined signal lines included in the cable assemblies 224 and 245 to the control portion 244e.

The reference clock generation portion 310 generates the reference clock signal to be the reference of the operation of the individual components of the endoscope system 1, and supplies the generated reference clock signal to the individual components of the endoscope system 1.

Next, a configuration of the light source device 4 will be described.

The light source device 4 includes a light source 41, a light source driver 42, a rotating filter 43, a drive portion 44, a driver 45, and a light source control portion 46.

The light source 41 is configured using a white LED (light emitting diode) or a xenon lamp or the like, and generates white light under the control of the light source control portion 46.

The light source driver 42 makes the light source 41 generate the white light by supplying a current to the light source 41 under the control of the light source control portion 46. The light generated by the light source 41 is radiated from the illumination lens window 24b of the distal end portion 24 through the rotating filter 43, a converging lens (not shown in the figure) and the light guide 241.

The rotating filter 43 is arranged on an optical path of the white light originated by the light source 41, and transmits only the light having a predetermined wavelength band for the white light originated by the light source 41 by rotating. Specifically, the rotating filter 43 includes a red filter 431, a green filter 432 and a blue filter 433 configured to transmit the light having respective wavelength bands of red light (R), green light (G) and blue light (B).

The rotating filter 43 sequentially transmits the light having the wavelength bands of red, green and blue (for example, red: 600 nm to 800 nm, green: 500 nm to 600 nm, blue: 400 nm to 500 nm) by rotating. Thus, for the white light originated by the light source 41, narrow-band light which is one of the red light, the green light and the blue light can be sequentially emitted to the endoscope 2.

The drive portion 44 is configured using a stepping motor or a DC motor or the like, and rotationally operates the rotating filter 43 with the synchronizing signals transmitted from the video processor 3 as the reference. The driver 45 supplies a predetermined current to the drive portion 44 under the control of the light source control portion 46.

The light source control portion 46 controls a current amount to be supplied to the light source 41 according to light adjustment signals transmitted from the light adjustment portion 304.

In addition, the light source control portion 46 rotates the rotating filter 43 by driving the drive portion 44 through the driver 45 under the control of the control portion 309.

The display device 5 has a function of receiving the in-vivo image generated by the video processor 3 through a video cable from the video processor 3 and displaying the in-vivo image. The display device 5 is configured using a liquid crystal or organic EL (electro luminescence) or the like.

Next, the laser device 6 will be described.

FIG. 3 is a main portion perspective view illustrating a state when the laser probe is inserted from the laser device to the endoscope system relating to the first embodiment, and FIG. 4 is a block diagram illustrating a functional configuration of the main portion when the laser probe connected to the laser device is inserted to the endoscope system relating to the first embodiment.

As illustrated in FIG. 3 and FIG. 4, in the present embodiment, to the endoscope 2 in the endoscope system 1, the laser probe 7 connected to the laser device 6 is inserted as described above.

The laser device 6 includes, as illustrated in FIG. 4, a YAG laser beam source 62 that generates the laser beam for breaking the target existing at a predetermined position of the object, and an aiming laser beam source 61 that generates the aiming monochromatic laser beam (hereinafter, the aiming laser beam) for confirming the laser irradiation position by the YAG laser.

In addition, the laser device 6 includes a turning mirror 67 disposed on the optical path of the YAG laser beam outputted from the YAG laser beam source 62, a turning mirror 66 disposed on the optical path of the aiming laser beam outputted from the aiming laser beam source 61, a focusing lens 65 configured to selectively radiate the YAG laser beam or the aiming laser beam, a control portion 63 configured to control the YAG laser beam source 62, the aiming laser beam source 61, the turning mirror 66, and the turning mirror 67, and an input portion 64 configured to provide the control portion 63 with predetermined input information of a switching operation of the laser beam or the like.

Then, in the laser device 6, by the control portion 63 according to a switching operation instruction from the input portion 64, the output of the YAG laser beam from the YAG laser beam source 62 and the output of the aiming laser beam from the aiming laser beam source 61 can be switched.

The laser probe 7 is connectable to the laser device 6 on the proximal end side, the distal end side is inserted from the treatment instrument insertion portion 222 in the endoscope 2, and the distal end portion 7a appears from the distal end opening portion 24c of the distal end portion 24 through the treatment instrument channel 247 of the distal end portion 24.

In addition, by being controlled by the control portion 63 in the laser device 6, the YAG laser beam or the aiming monochromatic laser beam can be radiated.

Next, a halation detection method when the aiming laser is radiated in the present embodiment will be described.

Figure 6:
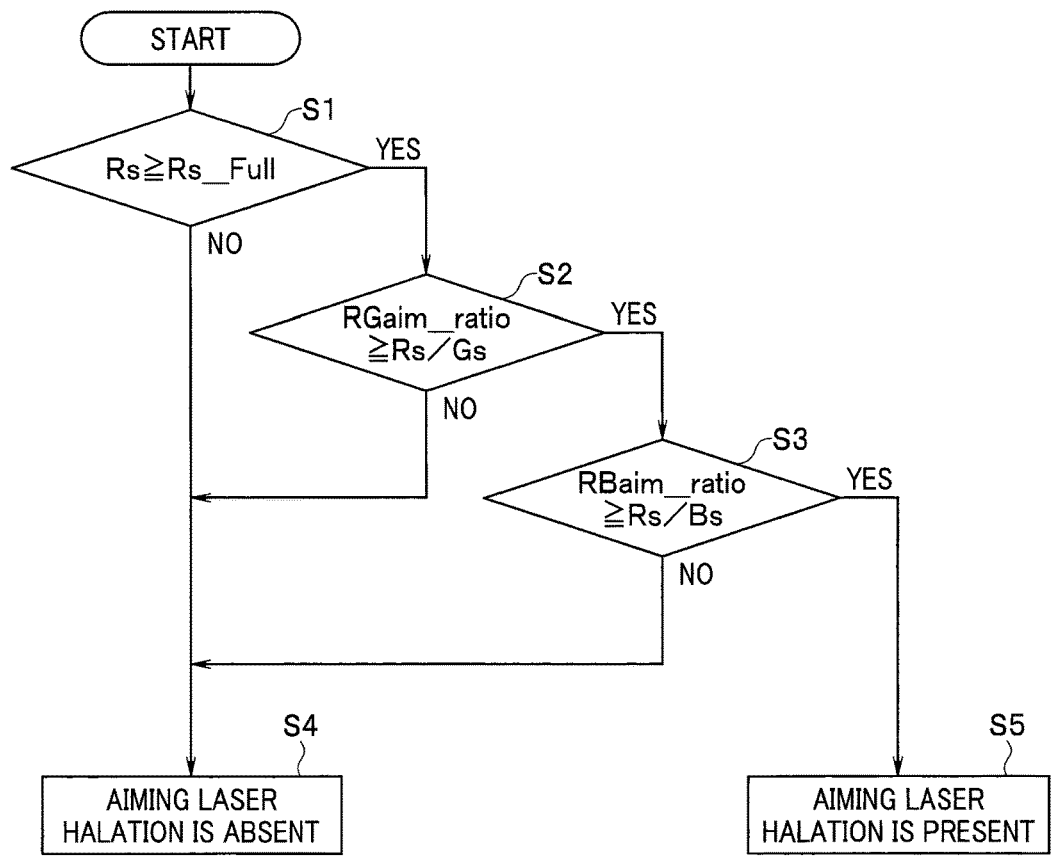
FIG. 6 is a flowchart illustrating a control action of an aiming laser halation detection portion in the endoscope system relating to the first embodiment.
Figure 7:
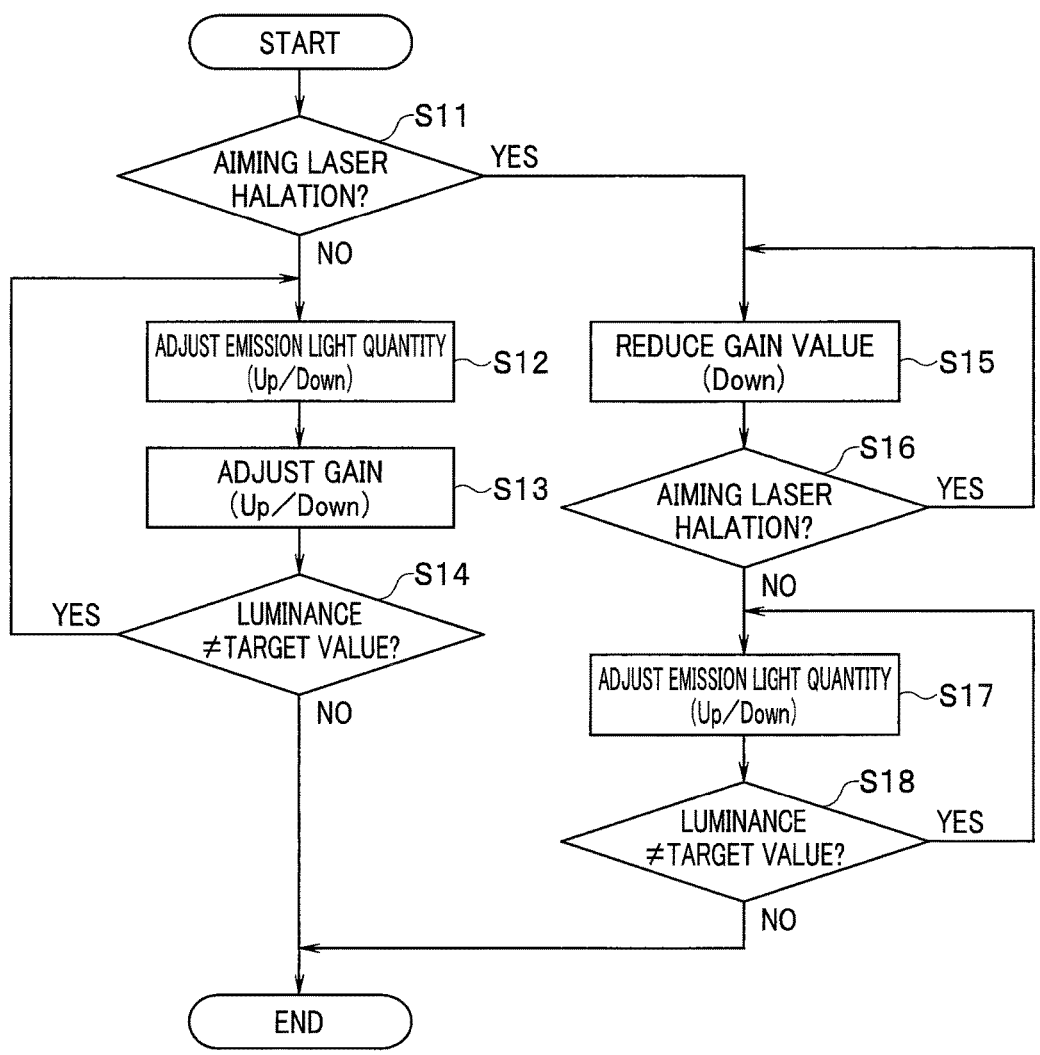
FIG. 7 is a flowchart illustrating a control action of a brightness detection portion in the endoscope system relating to the first embodiment.

FIG. 6 is a flowchart illustrating a control action of the aiming laser halation detection portion in the endoscope system relating to the first embodiment, and FIG. 7 is a flowchart illustrating a control action of the brightness detection portion in the endoscope system relating to the first embodiment.

The aiming laser halation detection portion 311 first holds the RGB image signals before being synchronized in the synchronization portion 302a respectively in the internal memory based on the timing control signals outputted from the control portion 309.

Then, as illustrated in FIG. 6, the aiming laser halation detection portion 311 detects whether or not the signal level "Rs" of R among the RGB image signals held in the internal memory has reached the stipulated level value "Rs_full" (step S1).

When the signal level "Rs" of R has not reached the stipulated level value "Rs_full" in step S1, the aiming laser halation detection portion 311 determines that the aiming laser halation is not generated (step S4).

On the other hand, in the case that the signal level "Rs" of R has reached the stipulated level value "Rs_full" in step S1, the aiming laser halation detection portion 311 determines that it is possible that the aiming laser halation is generated, and compares "Rs/Gs" which is the luminance level ratio of "Rs" and "Gs" with the stipulated level value "RGaim_ratio" next (step S2).

Here, when the luminance level ratio "Rs/Gs" is below the stipulated level value "RGaim_ratio", the aiming laser halation detection portion 311 determines that the aiming laser halation is not generated (step S4).

On the other hand, in the case that the luminance level ratio "Rs/Gs" is equal to or greater than the stipulated level value "RGaim_ratio" in step S2, the aiming laser halation detection portion 311 compares "Rs/Bs" which is the luminance level ratio of "Rs" and "Bs" with the stipulated level value "RBaim_ratio" (step S3).

Here, the aiming laser halation detection portion 311 determines that the aiming laser halation is not generated when the luminance level ratio "Rs/Bs" is below the stipulated level value "RBaim_ratio" (step S4), and determines that the aiming laser halation is generated when the luminance level ratio "Rs/Bs" is equal to or greater than the stipulated level value "RBaim_ratio" (step S5).

Figure 8:
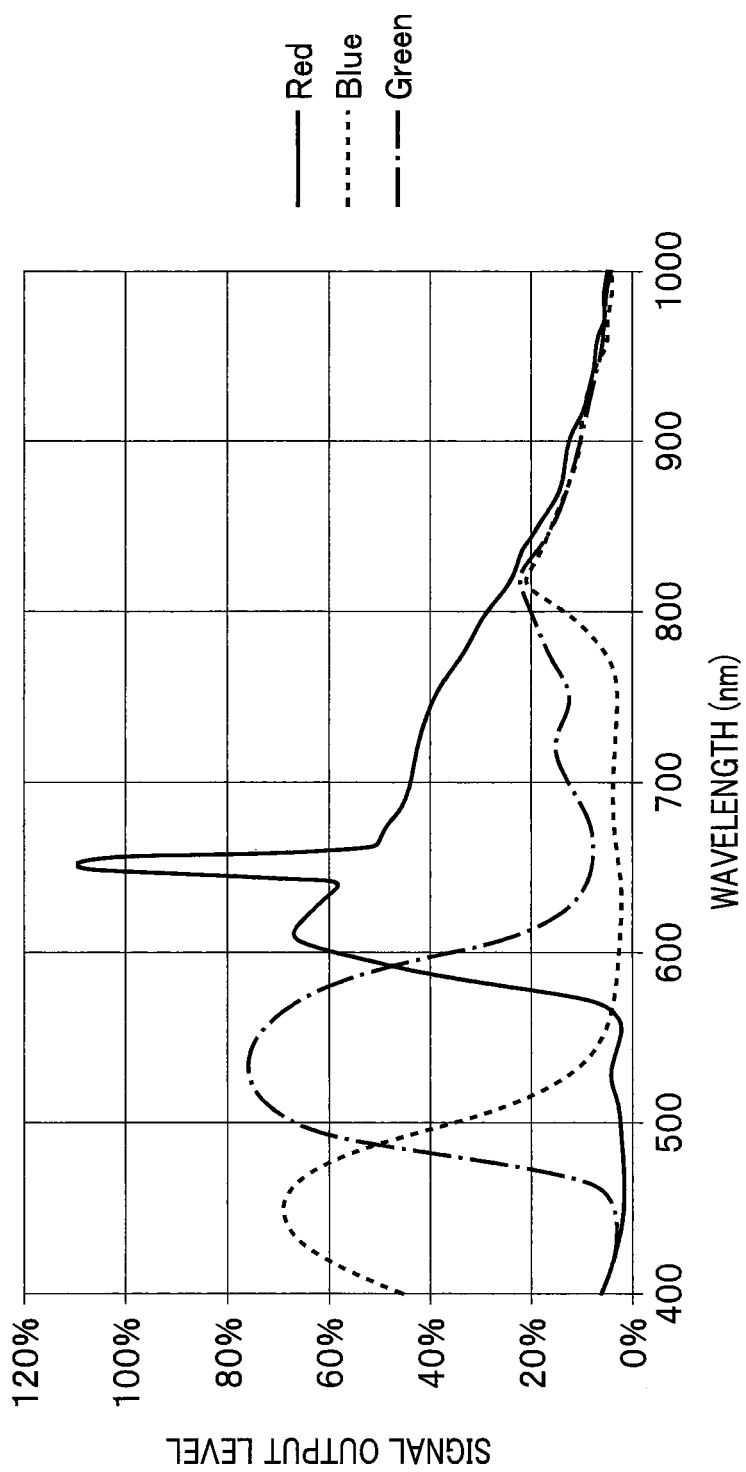
FIG. 8 is a diagram illustrating one example of an RGB signal output level when an aiming laser is radiated in a state that the laser probe is inserted from the laser device to the endoscope system relating to the first embodiment.

At the time, for the output level of the RGB image signals before being synchronized in the synchronization portion 302a, as illustrated in FIG. 8, only a signal output level of the light of an R wavelength of a narrow band relating to the aiming laser becomes extremely high, causing the halation as a result.

Then, when the halation by the aiming laser beam is detected, the aiming laser halation detection portion 311 outputs the halation information by the aiming laser to the brightness detection portion 303.

Next, light adjustment control by the brightness detection portion 303 in the present embodiment, the light adjustment control after the aiming laser halation is detected in particular, will be described.

FIG. 7 is the flowchart illustrating the control action of the brightness detection portion in the endoscope system relating to the first embodiment.

First, in the present embodiment, the brightness detection portion 303 detects the brightness level corresponding to the individual pixels from the RGB image signals held by the sample memory 302g, records the detected brightness level in the memory provided inside and also outputs the level to the control portion 309.

Then, under control of the control portion 309, the brightness detection portion 303 calculates the white balance adjustment value, the gain adjustment value and the light irradiation amount value to be the target brightness based on the detected brightness level, and outputs the white balance adjustment value to the white balance adjustment portion 302b, the gain adjustment value to the gain adjustment portion 302c, and the light irradiation amount value to the light adjustment portion 304.

Here, the output control of the gain adjustment value and the light irradiation amount value by the brightness detection portion 303 under the control of the control portion 309 is set to give the light irradiation amount value priority at normal time.

That is, under the control of the control portion 309, the brightness detection portion 303 performs the control to raise the light irradiation amount value in the case that the brightness lacks, and performs the control to raise the gain adjustment value in the case that the target value of the brightness is not reached yet.

On the other hand, in the present embodiment, the brightness detection portion 303 performs the control to change the ratio of the gain adjustment value and the light irradiation amount value in the light adjustment operation to perform the operation based on the halation information from the aiming laser halation detection portion 311.

That is, as illustrated in FIG. 7, in the case that the aiming laser halation detection portion 311 detects the halation (step S11), the output of the gain adjustment value is controlled so as to lower the gain value of the gain adjustment portion 302c first until the level of the aiming laser halation is lowered to the constant level (step S15). Note that, in step S15, the negative direction gain is applied depending on a situation.

Reduction of the gain adjustment value in step S15 is continued until the aiming laser halation detection portion 311 becomes the state of not detecting the halation (step S16).

Then, in steps S15 and S16, when the level of the aiming laser halation is lowered to the constant level by the adjustment of the gain adjustment value, the brightness detection portion 303 performs the control to raise the light irradiation amount value to be outputted to the light adjustment portion 304, under the control of the control portion 309 (step S17).

The adjustment of the light irradiation amount value in step S17 is continued until the brightness of the display image reaches the target luminance level (step S18).

On the other hand, in the case that the halation is not detected by the aiming laser halation detection portion 311 in step S11 (step S11), the brightness detection portion 303 performs normal light adjustment control under the control of the control portion 309 (step S12 to step S14).

Here, in the present embodiment, in the normal light adjustment control in the case that the aiming laser halation level described above is equal to or below the stipulated value, the brightness detection portion 303 does not perform the control described above (the gain of the gain adjustment portion 302c is the positive direction gain), and controls the gain adjustment value of the gain adjustment portion 302c and the light irradiation amount of the light adjustment portion 304 so that the brightness reaches the target level.

That is, for the output control of the gain adjustment value and the light irradiation amount value by the brightness detection portion 303, the light irradiation amount value is given priority, the control is performed to raise the light irradiation amount in the case that the brightness lacks (step S12), and the control is performed to raise the gain adjustment value in the case that the target value of the brightness is not reached yet (step S13).

Then, the brightness detection portion 303 outputs the white balance adjustment value, the gain adjustment value, and the light irradiation amount to the light adjustment portion 304.

As described above, the endoscope system of the first embodiment demonstrates an effect of being capable of strongly suppressing incident energy to the image sensor of the aiming laser beam without increasing a thickness of an optical filter (IR cut filter) loaded on a lens part of the image sensor, that is, being capable of improving visibility when the aiming laser is radiated without changing a size of an image sensor unit portion.

Second Embodiment

Next, a second embodiment of the present invention will be described.

While the endoscope system 1 of the first embodiment described above adopts the observation system of the so-called field sequential system, an endoscope system 101 of the present second embodiment adopts the observation system of the synchronous system.

Figure 9:
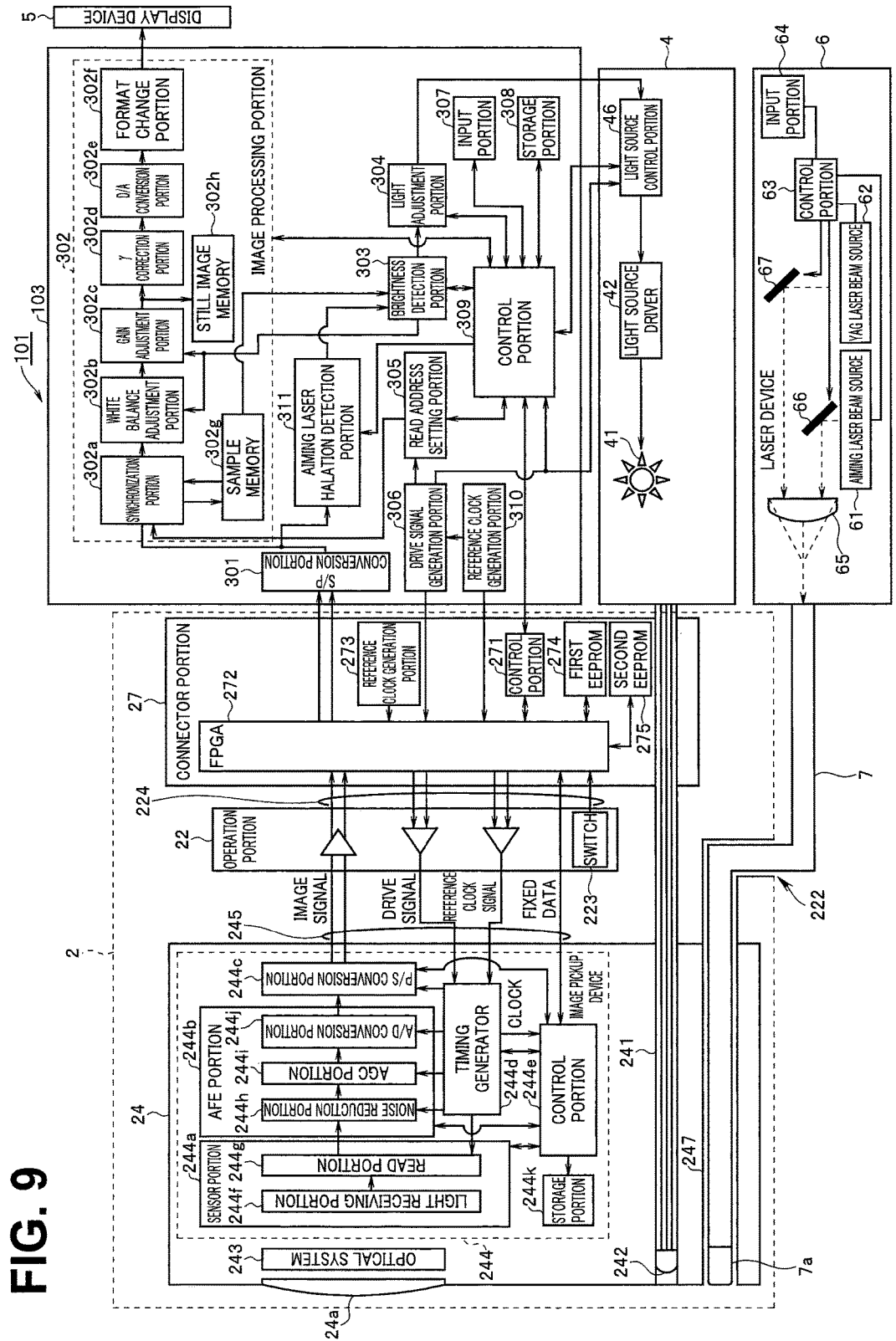
FIG. 9 is a block diagram illustrating a functional configuration of a main portion when the laser probe connected to the laser device is inserted to the endoscope system relating to a second embodiment of the present invention.

FIG. 9 is a block diagram illustrating a functional configuration of a main portion when the laser probe connected to the laser device is inserted to the endoscope system relating to the second embodiment of the present invention.

The basic configuration of the endoscope system 101 of the present second embodiment is similar to the endoscope system 1 of the first embodiment. Therefore, here, only differences from the first embodiment will be described, and descriptions of common parts will be omitted.

As illustrated in FIG. 9, similarly to the first embodiment, the endoscope system 101 of the present second embodiment includes: an endoscope 102 configured to pick up the in-vivo image of the object and output the image signal of the object image by inserting the distal end portion into the body cavity of the subject; a video processor 103 configured to execute the predetermined image processing to the image signals outputted from the endoscope 102 and generally control the operation of the entire endoscope system 101; a light source device 104 configured to generate the illumination light to be emitted from the distal end of the endoscope 102; and a display device 5 configured to display the image to which the image processing is executed in the video processor 103.

In addition, also in the second embodiment, to the endoscope 102, the laser probe 7 connected to the laser device 6 that generates the YAG laser beam and the aiming monochromatic laser beam, that is, the laser probe 7 capable of radiating the YAG laser beam and the aiming monochromatic laser beam is inserted.

Then, the endoscope system 101 of the present second embodiment adopts the observation system of the synchronous system as described above, and in the light receiving portion 244f in the image pickup device 244 of the endoscope 102, color filters of RGB three primary colors (not shown in the figure) corresponding to the individual pixels are disposed.

In addition, the light source device 104 is different from the light source device 4 in the first embodiment, and is configured including the light source 41, the light source driver 42, and the light source control portion 46.

Then, the light source 41 is configured using a white LED (light emitting diode) or a xenon lamp or the like, and generates the white light under the control of the light source control portion 46. In addition, the light source driver 42 makes the light source 41 generate the white light by supplying the current to the light source 41 under the control of the light source control portion 46. The light generated by the light source 41 is radiated from the distal end of the distal end portion 24 through the converging lens (not shown in the figure) and the light guide 241.

The light source control portion 46 controls the current amount to be supplied to the light source 41 according to the light adjustment signals transmitted from the light adjustment portion 304.

In addition, similarly to the first embodiment, in the second embodiment, the video processor 103 is configured including the S/P conversion portion 301, the image processing portion 302, the brightness detection portion 303, the light adjustment portion 304, the read address setting portion 305, the drive signal generation portion 306, the input portion 307, the storage portion 308, the control portion 309, the reference clock generation portion 310, and the aiming laser halation detection portion 311.

In addition, similarly to the first embodiment, the image processing portion 302 executes the predetermined image processing to the image signals of the parallel form outputted from the S/P conversion portion 301, and generates the in-vivo image to be displayed by the display device 5. In addition, the image processing portion 302 includes the synchronization portion 302a, the white balance (WB) adjustment portion 302b, the gain adjustment portion 302c, the γ correction portion 302d, the D/A conversion portion 302e, the format change portion 302f, the sample memory 302g, and the still image memory 302h.

In the present second embodiment, the synchronization portion 302a inputs the image signals inputted as the pixel information through the color filters in the image pickup device 244 described above to three memories (not shown in the figure) provided for each pixel, holds the values of the individual memories while successively updating the values corresponding to addresses of the pixels of the light receiving portion 244f read by the read portion 244g, and synchronizes the image signals of the three memories as the RGB image signals.

In addition, the synchronization portion 302a successively outputs the synchronized RGB image signals to the white balance adjustment portion 302b, and outputs part of RGB image signals to the sample memory 302g for the image analysis of the brightness detection or the like.

The white balance adjustment portion 302b, the gain adjustment portion 302c, the γ correction portion 302d, the D/A conversion portion 302e, the format change portion 302f, the sample memory 302g, and the still image memory 302h are similar to the first embodiment so that the descriptions here are omitted.

<Halation Detection Function when Aiming Laser is Radiated>

Next, the configuration relating to the halation detection function when the aiming laser is radiated in the video processor 103 will be described.

Similarly to the first embodiment, the aiming laser halation detection portion 311 is the circuit that detects the halation of the object when the aiming laser is radiated from the laser probe 7 inserted to the insertion channel 247 in the endoscope 102.

In addition, the aiming laser halation detection portion 311 holds the RGB image signals respectively in the internal memory based on the timing control signals outputted from the control portion 309 and the color filter array in the image pickup device 244 described above.

Further, similarly to the first embodiment, the signal levels of the RGB image signals held in the internal memory in the aiming laser halation detection portion 311 are defined as "Rs", "Gs" and "Bs" respectively, and the halation by the aiming laser of the "R" single color is detected from the luminance level ratios "Rs/Gs" and "Rs/Bs".

In addition, the stipulated level values "Rs_full", "RGaim_ratio" and "RBaim_ratio" similar to the above description are held (not shown in the figure) as the parameters inside the control portion 309 also in the present second embodiment.

Then, in the case that the R signal level "Rs" of the RGB image signals and the luminance level ratios "Rs/Gs" and "Rs/Bs" both exceed the stipulated level values described above, the aiming laser halation detection portion 311 detects the case as the halation by the aiming laser beam, and outputs the halation information by the aiming laser to the brightness detection portion 303.

<Brightness Control Function when Aiming Laser is Radiated>

The configuration relating to the brightness control function when the aiming laser is radiated in the video processor 103 in the present second embodiment is similar to the first embodiment, and also in the present second embodiment, the brightness detection portion 303 performs the control to change the ratio of the gain adjustment value and the light irradiation amount value in the light adjustment operation to perform the operation based on the halation information from the aiming laser halation detection portion 311.

That is, in the case that the aiming laser halation detection portion 311 detects the halation, under the control of the control portion 309, the brightness detection portion 303 controls the output of the gain adjustment value so as to lower the gain of the gain adjustment portion 302c (apply the negative direction gain depending on the situation) until the level of the aiming laser halation is lowered to the constant level, and raises the light irradiation amount value to be outputted to the light adjustment portion 304, thereby performing the control to turn the brightness of the display image to the target level.

Further, the brightness detection portion 303 does not perform the control described above (the gain of the gain adjustment portion 302c is the positive direction gain) in the case that the aiming laser halation level is equal to or below the stipulated value, and controls the gain adjustment value of the gain adjustment portion 302c and the light irradiation amount of the light adjustment portion 304 so that the brightness reaches the target level.

In addition, under the control of the control portion 309, the light adjustment portion 304 sets the light quantity or the like of the light generated by the light source device 104 based on the light irradiation amount value calculated by the brightness detection portion 303, and transmits the set condition to the light source device 104.

The control portion 309 is configured using a CPU or the like, and performs the drive control of the individual components including the video processor 103 (the aiming laser halation detection portion 311 in particular), the endoscope 102 and the light source device 104, and input/output control of the information to the individual components or the like.

In addition, the control portion 309 transmits the setting data for the image pickup control to the FPGA 272 of the connector portion 27 in the endoscope 102 connected to the video processor 103, and transmits the signals and the data needed for the image pickup device 244 through the predetermined signal lines included in the cable assemblies 224 and 245 to the control portion 244e.

The other configuration of the video processor 103 and the configurations of the display device 5 and the laser device 6 or the like are similar to the first embodiment so that the descriptions here are omitted.

Next, the halation detection method when the aiming laser is radiated in the present second embodiment and the light adjustment control after the aiming laser halation is detected will be described.

The aiming laser halation detection portion 311 first holds the RGB image signals respectively in the internal memory based on the timing control signals outputted from the control portion 309 and the color filter array in the image pickup device 244 described above.

Thereafter, similarly to the first embodiment, the aiming laser halation detection portion 311 detects whether or not the signal level "Rs" of R among the RGB image signals held in the internal memory has reached the stipulated level value "Rs_full" (see step S1 in FIG. 6), and in the case that the signal level "Rs" of R has reached the stipulated level value "Rs_full" and the luminance level ratios "Rs/Gs" and "Rs/Bs" are equal to or greater than the stipulated level value, determines that the aiming laser halation is generated (see steps S2, S3 and S5 in FIG. 6).

Then, when the halation by the aiming laser beam is detected, the aiming laser halation detection portion 311 outputs the halation information by the aiming laser to the brightness detection portion 303, the output of the gain adjustment value is controlled so as to lower the gain value of the gain adjustment portion 302c first until the level of the aiming laser halation is lowered to the constant level (see steps S15 and S16 in FIG. 7), and when the level of the aiming laser halation is lowered to the constant level by the adjustment of the gain adjustment value, the brightness detection portion 303 performs the control to raise the light irradiation amount value to be outputted to the light adjustment portion 304 under the control of the control portion 309 (see step S17 in FIG. 7).

The adjustment of the light irradiation amount value in step S17 is continued until the brightness of the display image reaches the target luminance level (see step S18 in FIG. 7).

On the other hand, in the case that the halation is not detected by the aiming laser halation detection portion 311, the brightness detection portion 303 performs the normal light adjustment control under the control of the control portion 309 (see step S12 to step S14 in FIG. 7).

As described above, the endoscope system of the present second embodiment demonstrates, similarly to the first embodiment, the effect of being capable of strongly suppressing the incident energy to the image sensor of the aiming laser beam without increasing the thickness of the optical filter (IR cut filter) loaded on the lens part of the image sensor, that is, being capable of improving the visibility when the aiming laser is radiated without changing the size of an image sensor unit portion.

Note that, while the function relating to the aiming laser halation detection portion 311 described above is provided in the video processor 3 (103) in the embodiments described above, without being limited to that, the configuration of providing the function in the image pickup device 244, the operation portion 22 or the connector portion 27 in the endoscope 2 (102) for example is also included in the present invention.

Further, while the configuration of the endoscope system is exemplified as the embodiment of the present invention in the embodiments described above, the present invention is not limited to that, and the present invention is applicable also to other image pickup systems including an image processing function.

The present invention is not limited to the embodiments described above, and can be variously changed, modified or the like without changing a gist of the present invention.

According to the present invention, it is possible to provide the endoscope system capable of improving the visibility when the aiming laser is radiated without changing the size of the image sensor unit portion.

What is claimed is:

1. An endoscope system comprising:
    an endoscope including an image pickup sensor configured to pick up an image of an object;
    an illumination lens configured to irradiate the object with illumination light;
    an insertion channel provided in the endoscope and configured to allow insertion of at least a laser probe capable of irradiating a predetermined position of the object with an aiming monochromatic laser beam for confirming a laser irradiation position; and
    a processor including hardware, the processor being configured to:
        control an illumination light intensity and an irradiation time period from the illumination lens;
        control a gain of an image pickup signal outputted from the image pickup sensor;
        detect whether or not halation relating to the object is generated when the aiming monochromatic laser beam is radiated; and
        where generation of the halation by the aiming monochromatic laser beam is detected, perform a control to lower a color gain of a color component of the illumination light that is same as a color component of the aiming monochromatic laser beam, and perform a control to raise a light quantity of the illumination light including a wavelength of the aiming monochromatic laser beam.

* * * * *